US010543380B2

(12) United States Patent
Uhlemann et al.

(10) Patent No.: US 10,543,380 B2
(45) Date of Patent: Jan. 28, 2020

(54) ALIGNMENT OF THE COORDINATE SYSTEMS OF EXTERNAL BEAM RADIOTHERAPY AND MAGNETIC RESONANCE IMAGING SYSTEMS

(71) Applicant: KONINKLIJKE PHILIPS N.V., Eindhoven (NL)

(72) Inventors: Falk Uhlemann, Eindhoven (NL); Johannes Adrianus Overweg, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 961 days.

(21) Appl. No.: 15/025,302

(22) PCT Filed: Sep. 22, 2014

(86) PCT No.: PCT/EP2014/070079
§ 371 (c)(1),
(2) Date: Mar. 28, 2016

(87) PCT Pub. No.: WO2015/044065
PCT Pub. Date: Apr. 2, 2015

(65) Prior Publication Data
US 2016/0213951 A1    Jul. 28, 2016

(30) Foreign Application Priority Data

Sep. 30, 2013 (EP) ..................................... 13186655

(51) Int. Cl.
*A61N 5/10* (2006.01)
*A61B 5/00* (2006.01)
*A61B 5/055* (2006.01)

(52) U.S. Cl.
CPC .......... *A61N 5/1049* (2013.01); *A61B 5/0035* (2013.01); *A61B 5/0555* (2013.01);
(Continued)

(58) Field of Classification Search
CPC ...... A61N 5/10; A61N 5/1049; A61N 5/0035; A61N 5/0555
See application file for complete search history.

(56) References Cited

U.S. PATENT DOCUMENTS 6,519,316 B1    2/2003 Collins
2007/0195936 A1    8/2007 Manthey et al.
(Continued)

FOREIGN PATENT DOCUMENTS

CN    102631215 A    8/2012
WO    2009012577 A1    1/2009
(Continued)

*Primary Examiner* — Joseph M Santos Rodriguez
(74) *Attorney, Agent, or Firm* — Sherry Austin (57) ABSTRACT

The invention provides for a medical instrument (200, 300, 400, 500, 600, 700) comprising a magnetic resonance imaging system (204) operable for acquiring magnetic resonance data (266) from a subject (236) within an imaging zone (232) and an external beam radiotherapy system (202) operable for irradiating a target zone (238) within the imaging zone. The medical instrument further has a radiation beam generation system (208, 302, 302', 302") operable for generating a radiation beam (242, 304, 304', 304") and a radiation beam detection system (243, 502, 502') operable for acquiring radiation beam detection data (270) descriptive of the radiation beam. Instructions cause a processor (248) controlling the instrument to receive (100) planning data (260) descriptive of a spatially dependent radiation dose and generate (102) external beam radiotherapy control commands (264) using the radiation dose. The instructions causes the processor to repeatedly: control (106) the external beam radiotherapy system to irradiate the target zone using the external beam radiotherapy system control commands; generate (108) the radiation beams using the radiation beam generation system; measure (110) the radiation beam detection data using the radiation beam detection system; acquire (112) the magnetic resonance imaging data using the magnetic resonance imaging system, generate (114) a magnetic resonance image (268) using the magnetic resonance image data, determine (116) a registration (274) of the magnetic resonance image to the radiation beam detection data; calculate (118) a mapping (276) using the registration; and modify the external beam radiotherapy system control commands using the mapping.

14 Claims, 7 Drawing Sheets

(52) U.S. Cl.
CPC ......... *A61N 5/1039* (2013.01); *A61N 5/1067* (2013.01); *A61N 5/1071* (2013.01); *A61N 5/1077* (2013.01); *A61B 2576/00* (2013.01); *A61N 2005/1054* (2013.01); *A61N 2005/1055* (2013.01); *A61N 2005/1074* (2013.01); *A61N 2005/1087* (2013.01); *A61N 2005/1089* (2013.01)

(56) References Cited

U.S. PATENT DOCUMENTS

| | | |
|---|---|---|
| 2008/0208036 A1 | 8/2008 | Amies et al. |
| 2010/0239066 A1 | 9/2010 | Fahrig et al. |
| 2012/0035462 A1 | 2/2012 | Maurer |
| 2013/0006036 A1 | 1/2013 | Raleigh et al. |

FOREIGN PATENT DOCUMENTS

| | | |
|---|---|---|
| WO | 2011008969 A1 | 1/2011 |
| WO | 2012080948 A1 | 6/2012 |

ALIGNMENT OF THE COORDINATE SYSTEMS OF EXTERNAL BEAM RADIOTHERAPY AND MAGNETIC RESONANCE IMAGING SYSTEMS

CROSS REFERENCE TO RELATED APPLICATIONS

This application is a U.S. national phase application of International Application No. PCT/EP2014/070079, filed on Sep. 22, 2014, which claims the benefit of EP Application Serial No. 13186655.0 filed on Sep. 30, 2013 and is incorporated herein by reference.

TECHNICAL FIELD

The invention relates to external beam radiotherapy, in particular to image guided external beam radiotherapy.

BACKGROUND OF THE INVENTION

In routine practice of Radiotherapy (RT), the subject is positioned relative to the stationary center of the rotating arc carrying the RT source. Positioning implies both height and lateral adjustment of the subject table. This positioning is required to optimize the dose in the lesion beyond variation that can be obtained by applying RT rays from different angles.

Integration of MR (Magnetic Resonance) and Linear Accelerators (LINAC) opens new horizons in Radiotherapy by improved lesion targeting, especially for moving organs. In a practical implementation proposal, the LINAC rotates around the subject to hit the gross target volume (GTV) and clinical target volume (CTV) from multiple angles while minimizing the radiation exposure for surrounding tissues.

The combination of magnetic resonance apparatuses and LINAC radiotherapy sources is known. Typically a LINAC source is placed on a rotating gantry about the magnet and the magnet designed such that the LINAC rotates in a zero-field region of the magnet.

International patent application WO 2009/012577 A1 discloses the use of portal imaging to modify treatment parameters during radiotherapy.

SUMMARY OF THE INVENTION

The invention provides for a medical instrument, a computer program product and a method in the independent claims. Embodiments are given in the dependent claims.

As will be appreciated by one skilled in the art, aspects of the present invention may be embodied as an apparatus, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer executable code embodied thereon.

Any combination of one or more computer readable medium(s) may be utilized. The computer readable medium may be a computer readable signal medium or a computer readable storage medium. A 'computer-readable storage medium' as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example a data may be retrieved over a modem, over the internet, or over a local area network. Computer executable code embodied on a computer readable medium may be transmitted using any appropriate medium, including but not limited to wireless, wireline, optical fiber cable, RF, etc., or any suitable combination of the foregoing.

A computer readable signal medium may include a propagated data signal with computer executable code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

'Computer memory' or 'memory' is an example of a computer-readable storage medium. Computer memory is any memory which is directly accessible to a processor. 'Computer storage' or 'storage' is a further example of a computer-readable storage medium. Computer storage is any non-volatile computer-readable storage medium. In some embodiments computer storage may also be computer memory or vice versa.

A 'processor' as used herein encompasses an electronic component which is able to execute a program or machine executable instruction or computer executable code. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. The computer executable code may be executed by multiple processors that may be within the same computing device or which may even be distributed across multiple computing devices.

Computer executable code may comprise machine executable instructions or a program which causes a processor to perform an aspect of the present invention. Computer executable code for carrying out operations for aspects of the present invention may be written in any combination of one or more programming languages, including an object oriented programming language such as Java, Smalltalk, C++ or the like and conventional procedural programming languages, such as the "C" programming language or similar programming languages and compiled into machine executable instructions. In some instances the computer executable code may be in the form of a high level language or in a pre-compiled form and be used in conjunction with an interpreter which generates the machine executable instructions on the fly.

The computer executable code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described with reference to flowchart illustrations and/or block diagrams of methods, apparatus (systems) and computer program products according to embodiments of the invention. It will be understood that each block or a portion of the blocks of the flowchart, illustrations, and/or block diagrams, can be implemented by computer program instructions in form of computer executable code when applicable. It is further under stood that, when not mutually exclusive, combinations of blocks in different flowcharts, illustrations, and/or block diagrams may be combined. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, gamepad, webcam, headset, gear sticks, steering wheel, pedals, wired glove, dance pad, remote control, and accelerometer are all examples of user interface components which enable the receiving of information or data from an operator.

A 'hardware interface' as used herein encompasses an interface which enables the processor of a computer system to interact with and/or control an external computing device and/or apparatus. A hardware interface may allow a processor to send control signals or instructions to an external computing device and/or apparatus. A hardware interface may also enable a processor to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, Bluetooth connection, Wireless local area network connection, TCP/IP connection, Ethernet connection, control voltage interface, MIDI interface, analog input interface, and digital input interface.

A 'display' or 'display device' as used herein encompasses an output device or a user interface adapted for displaying images or data. A display may output visual, audio, and or tactile data. Examples of a display include, but are not limited to: a computer monitor, a television screen, a touch screen, tactile electronic display, Braille screen, Cathode ray tube (CRT), Storage tube, Bistable display, Electronic paper, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, and Head-mounted display.

Magnetic Resonance (MR) data is defined herein as being the recorded measurements of radio frequency signals emitted by atomic spins by the antenna of a Magnetic resonance apparatus during a magnetic resonance imaging scan. Magnetic resonance data is an example of medical image data. A Magnetic Resonance Imaging (MRI) image is defined herein as being the reconstructed two or three dimensional visualization of anatomic data contained within the magnetic resonance imaging data. This visualization can be performed using a computer.

In one aspect the invention provides for a medical instrument. The medical instrument comprises a magnetic resonance imaging system operable for acquiring magnetic resonance data from a subject within an imaging zone. The magnetic resonance imaging system has a first coordinates system. Magnetic resonance imaging systems function by producing a large static magnetic field within the imaging zone. Spatial encoding is performed by the use of so called gradient coils or a system of gradient coils. The position of the gradient coils defines the intrinsic coordinates system for the acquired magnetic resonance data. The medical instrument further comprises an external beam radio therapy system operable for irradiating a target zone. The target zone is within the imaging zone. The external beam radiotherapy system has a second coordinates system. The external beam radiotherapy system may be used to controllably direct radiation to irradiate the target zone. The controls and systems used for directing the radiation defines the second coordinates system.

The medical instrument further comprises a radiation beam generation system operable for generating a radiation beam. The radiation beam generation system as used herein encompasses any system which may be used for generating a beam of radiation that is ionizing. For instance the radiation beam generation system may encompass an X-ray or gamma ray system. The radiation beam generation system may also encompass charged particles such as protons or charged nuclei. In some embodiments the radiation beam generation system is a separate component and in other embodiments the external beam radiotherapy system is a part of the radiation beam generation system.

The medical instrument further comprises a radiation beam detection system operable for acquiring radiation beam detection data descriptive of the radiation beam in the second coordinate system. The radiation beam detection system may in other words be operable for detecting the presence or other properties of the radiation beam. Notably, according to the invention the radiation beam detection system is configured to detect an image carried by the radiation beam. That is the radiation beam detection data descriptive of the radiation beam in the second coordinate system are acquired in the form of image data. The medical instrument further comprises a memory for storing machine-executable instructions. The medical instrument further comprises a processor for executing the machine-executable instructions. The execution of the machine-executable instructions enables the processor to control or operate the medical instrument and its various components.

Execution of the instructions causes the processor to receive planning data descriptive of a spatially dependent radiation dose to the target zone. The planning data may contain a mapping which indicates the amount of radiation to be delivered to various portions of the target zone. In some instances the planning data may also contain references to anatomical zones or portions of the subject which are to be not irradiated or have a minimal amount of radiation. Execution of the instructions further cause the processor to generate external beam radiotherapy control commands using the spatially dependent radiation dose. In this step the spatially dependent radiation dose is used to generate specific commands which are then used by the processor to control the external beam radiotherapy system to irradiate the target zone.

Execution of the instructions may also cause the processor to acquire preliminary magnetic resonance data which is used to reconstruct a preliminary magnetic resonance image. The preliminary magnetic resonance image could for instance be registered to the planning data and used with the spatially dependent dose to generate the external beam radiotherapy control commands.

Likewise the magnetic resonance image reconstructed from magnetic resonance data that is acquired repeatedly during the irradiation of the target zone may also be registered to the spatially dependent radiation dose. This registration may be used with the mapping to modify the external beam radiotherapy system control commands. This provides for magnetic resonance guidance of the external beam radiotherapy system.

In another embodiment execution of the instructions further cause the processor to repeatedly control the external beam radiotherapy system to irradiate the target zone using the external beam radiotherapy system control commands. In this step the external beam radiotherapy system control commands are used by the processor to control the external beam radiotherapy system to irradiate the target zone. Execution of the instructions further cause the processor to repeatedly generate the radiation beam using the radiation beam generation system. The generation of the radiation beam using the radiation beam generation system could be performed sequentially with irradiation of the target zone or in some embodiments they could be performed concurrently. Execution of the instructions further cause the processor to repeatedly measure the radiation beam detection data using the radiation beam detection system.

Execution of the instructions further cause the processor to repeatedly acquire the magnetic resonance imaging data using the magnetic resonance imaging system. Execution of the instructions further cause the processor to repeatedly generate a magnetic resonance image using the magnetic resonance image data. Execution of the instructions further cause the processor to repeatedly register the magnetic resonance image to the radiation beam detection data. In this step the magnetic resonance image and the radiation beam detection data are used to find mapping or correlation between the coordinates of these two images or data. The radiation beam detection data may take various forms. In some instances it may be an image such as a portal image or it may just be raw data that has been collected from a sensor array. In any case the magnetic resonance image and its registration to the radiation beam detection data defines a coordinate transformation between the two.

Execution of the instructions further cause the processor to repeatedly calculate a mapping between the first coordinates system and the second coordinates system using at least partially the registration. Execution of the instructions further cause the processor to repeatedly modify the external beam radiotherapy system control commands using the mapping. The medical instrument may be used to guide or control the external beam radiotherapy system using the magnetic resonance imaging system. However, during the course of performing the irradiation of the target zone there may be a drift or change between the first coordinates system and the second coordinates system. For instance various components may heat up and may cause spatial changes which may cause a minor misalignment between the first coordinates system and the second coordinates system. Shifts in of the MR image information can also be caused by changes in the strength of the local magnetic field, which may be caused by drifts in the MR field generation system or by changes in the magnetic effect of the patient. An apparent shift of the image can also be caused by frequency drift in the local oscillator of the MR system. An important aspect of the shift of the MR coordinate system is that the magnitude of the shift depends on the characteristics of the MR imaging sequence, in particular on the strength of the read-out gradient strength. Therefore it is beneficial if the sequence used for guiding the treatment process is sufficiently similar to the sequence used for aligning the coordinate systems that both sequences exhibit the same coordinate system shift. A shift of the MR coordinate system relative to the treatment system coordinate system will be a disadvantage because errors in the alignments of the first and second coordinates system may result in errors in irradiating the subject. For instance a region outside the target zone may be irradiated instead of the target zone. This embodiment may be beneficial because the magnetic resonance image and the radiation beam detection data are used to calculate a mapping between the first coordinates system and the second coordinates system which may be used to determine a spatial correction is then used to modify the external beam radiotherapy system to control the irradiation of the target zone more accurately.

Radiation beam as used herein may encompass an X-ray beam or a gamma radiation. Radiation beam may also refer to beams of protons or charged particles.

The mapping may also be used for modifying the acquisition of the magnetic resonance data. For instance the location of a particular slice of data which is acquired may be adjusted using knowledge of how the systems have changed relative to one another.

In another embodiment the external beam radiotherapy system comprises a radiation beam source for irradiating the target zone. The radiation beam generation system comprises the radiation beam source. The radiation beam detection system comprises a portal imaging system for acquiring a portal image of the subject using the radiation beam. The radiation beam detection data comprises the portal image. Execution of the instructions further causes the processor to at least partially calculate the mapping by registering the portal image to the magnetic resonance image. The magnetic resonance image is determined by the position of the gradient coils and the position of the portal image is determined by the position of the portal imaging system. The portal imaging system is typically mounted directly to the external beam radiotherapy system. Therefore, the magnetic resonance image and the portal image may be used to determine the relative coordinates between the magnetic resonance imaging system and the external beam radiotherapy system. The portal imaging system has a predefined mechanical relationship with the external beam radiotherapy system. This provides a more reliable mapping between the coordinate systems. Notably the mapping can be determined with the subject to be treated in place. Hence, the calibration of the mapping can be integrated in the treatment procedure. Moreover, the calibration of the mapping is not sensitive to changes that may occur during positioning of the subject.

Execution of the instructions further cause the processor to control the external beam radiotherapy system to acquire the portal image using the radiation passing through the subject.

In another embodiment execution of the instructions further cause the process to repeatedly identify an anatomical landmark of the subject in the portal image. Execution of the instructions further causes the processor to identify the anatomical landmark in the magnetic resonance image. This may be done repeatedly. The registration of the portal image to the magnetic resonance image is performed at least partially using the anatomical landmark.

In another embodiment the anatomical landmark is any one of the following: a bone to soft tissue transition, an implanted fiducial marker, and an external surface of the subject. In the case where the portal imaging is of low resolution it may be difficult to identify an internal anatomical landmark. However, a silhouette in a portal image may be very useful for identifying the position of the subject in both the portal image and the magnetic resonance image. In this way the external surface of the subject may be used to determine the mapping.

In another embodiment the magnetic resonance imaging system comprises a subject support. The subject support comprises a phantom. The phantom comprises at least one reference point identifiable in the portal image and the magnetic resonance image. Alternatively the phantom contains one object visible in the MR image and another object visible in the portal image, with a precise geometric relationship between these two objects. It may be beneficial if the MR-visible object is made from and surrounded by material with a low magnetic susceptibility, such that the magnetic field inside the MR-visible fiducial is essentially equal to the field inside the patient. It may also be beneficial if the difference in field between the inside of the fiducal and the field in the patient is smaller than the field difference between two adjacent pixels generated by the read-out gradient. It may also be beneficial for the MR-visible fiducial to be placed at sufficient distance from electrically conducing objects, because the magnetic fields generated by induced currents in such objects may cause an apparent shift in the position of the MR-visible fiducial. Execution of the instructions further causes the processor to at least partially calculate the mapping by registering the at least one reference point in the portal image to the at least one reference point in the magnetic resonance image. A subject support as used herein encompasses an object for supporting a subject or a portion of a subject. The subject support may also be referred to as a fixation.

In another embodiment the radiation beam generation system comprises a narrow beam X-ray generator for generating a narrow beam X-ray. The narrow beam X-ray generator is attached to the magnetic resonance imaging system. The memory comprises a spatial calibration descriptive of the path of the narrow beam X-ray relative to the field of view of the magnetic resonance imaging system. The Radiation beam detection system is mounted on the external beam radiotherapy system. The Radiation beam detection data is descriptive of the path of the narrow ray beam through the X-ray detection system. There may also be a second spatial calibration which is descriptive of the position of the Radiation beam detection system relative to the second coordinates system.

The spatial calibration descriptive of the path of narrow beam X-ray relative to the field of view of the magnetic resonance imaging system may also be interpreted as being relative to the first coordinates system. In this embodiment an X-ray generator, which is separate from the external beam radiotherapy system, is used to generate an X-ray beam which is then detected by the radiation beam detection system. The path of the X-ray beam is known relative to the first coordinates system. The measurement of the path of the X-ray beam as measured by the radiation beam detection system is known relative to the second coordinates system. This enables a mapping to be determined between the first coordinates system and the second coordinates system.

There may be several different types of narrow beam X-ray sources. For instance a very small or miniature X-ray tube may be used, also so called nanotube X-ray generators.

In another embodiment the magnetic resonance imaging system is operable for supporting the subject away from the path of the narrow beam X-ray. This embodiment is interpreted in that the path of the narrow beam X-ray does not go through the subject. This may be advantageous because the subject is not irradiated by the narrow beam X-ray generator.

In another embodiment the radiation beam detection system comprises a portal imaging system for acquiring a portal image of the subject during irradiation of the target zone using the external beam radiotherapy system. The portal imaging system is operable for detecting the narrow beam X-ray. Execution of the instructions further causes the processor to at least partially calculate the mapping by registering the portal image to the spatial calibration.

In another embodiment the Radiation beam detection system further comprises an X-ray detector sensor array operable for detecting the path of the narrow beam X-ray through the X-ray detection sensor. For instance the X-ray detection sensor may be a linear or two-dimensional array which can detect where the narrow beam X-ray beam would pass through the X-ray detection sensor array.

In another embodiment the external beam radiotherapy system has an iso-center. The modified external beam radiotherapy system control commands cause the external beam radiotherapy system to align the iso-center with the target zone. For instance a mechanical table may be used to change the position of the external beam radiotherapy system. In other embodiments the subject may be reposing on a subject support which can be moved. In this case the subject support may be moved such that the target zone lies on the iso-center of the external beam radiotherapy system.

In another embodiment execution of the instructions cause the processor to perform any one of the following: control of the external beam radiotherapy system to halt irradiating the target zone if the mapping indicates a difference between the first coordinates system and the second coordinates system that is greater than a first predetermined threshold, display a warning message on a display, automatically adjust the radiation of the external beam radiotherapy system, automatically adjust the acquisition of the magnetic resonance imaging data, control the external beam radiotherapy system to halt irradiating the target zone if a temporal change in the mapping is greater than a second predetermined threshold, and combinations thereof.

In another embodiment the external beam radiotherapy system is a proton beam system.

In another embodiment the external beam radiotherapy system is a charged particle beam system.

In another embodiment the external beam radiotherapy system is a linear accelerator (LINAC). Notably, the external radiotherapy system includes a LINAC which generates a high-energy electron beam emitted from a cathode and impinging onto an anode target. The high-energy electron beam causes a high-energy x-ray beam or a y-ray beam. The high-energy x-ray beam or the y-ray beam have a therapeutic effect on that their ionising effect may destroy tissue of a lesion or cancerous tissue.

In another aspect the invention provides for a computer program product comprising machine-executable instructions for execution by a processor controlling the medical instrument. The medical instrument comprises a magnetic resonance imaging system operable for acquiring magnetic resonance data from a subject within an imaging zone. The magnetic resonance imaging system has a first coordinates system. The medical instrument further comprises an external beam radiotherapy system operable for irradiating a target zone. The target zone is within the imaging zone. The external beam radiotherapy system has a second coordinates system.

The medical instrument further comprises a radiation beam generation system operable for generating a radiation beam. The medical instrument further comprises a radiation beam detection system operable for acquiring radiation beam detection data descriptive of the radiation beam in the second coordinate system. Execution of the instructions causes the processor to receive planning data descriptive of a partially dependent radiation dose to the target zone. Execution of the instructions further cause the processor to generate external beam radiotherapy control commands using the spatially dependent radiation dose. Execution of the instructions causes the processor to repeatedly control the external beam radiotherapy system to irradiate the target zone using the external beam radiotherapy system control commands. Execution of the instructions further cause the processor to repeatedly generate the radiation beam using the radiation beam generation system.

Execution of the instructions further cause the processor to measure the radiation beam detection data using the radiation beam detection system. Execution of the instructions further cause the processor to acquire the magnetic resonance imaging data using the magnetic resonance imaging system. Execution of the instructions further cause the processor to generate a magnetic resonance image using the magnetic resonance image data. Execution of the instructions further cause the processor to repeatedly register the magnetic resonance image to the radiation beam detection data. Execution of the instructions further cause the processor to calculate a mapping between the first coordinates system and the second coordinates system using at least partially the registration. Execution of the instructions further cause the processor to repeatedly modify the external beam radiotherapy system control commands using the mapping.

In another aspect the invention provides for a method of operating a medical instrument. The medical instrument comprises a magnetic resonance imaging system operable for acquiring magnetic resonance data from a subject within an imaging zone. The magnetic resonance imaging system has a first coordinates system. The instrument further comprises an external beam radiotherapy system operable for irradiating a target zone. The target zone is within the imaging zone. The external beam radiotherapy system has a second coordinates system. The instrument further comprises a radiation beam generation system operable for generating a radiation beam. The instrument further comprises a radiation beam detection system operable for acquiring radiation beam detection data descriptive of the radiation beam in the second coordinate system. The method comprises receiving planning data descriptive of a spatially dependent radiation dose to the target zone.

The method further comprises generating external beam radiotherapy control commands using the spatially dependent radiation dose. The method further comprises repeatedly controlling the external beam radiotherapy system to irradiate the target zone using the external beam radiotherapy system control commands. The method further comprises repeatedly generating the radiation beam using the radiation beam generation system. The method further comprises repeatedly measuring the radiation beam detection data using the radiation beam detection system. The method further comprises repeatedly acquiring the magnetic resonance imaging data using the magnetic resonance imaging system. The method further comprises repeatedly generating a magnetic resonance image using the magnetic resonance image data. The method further comprises repeatedly registering the magnetic resonance image to the radiation beam detection data. The method further comprises repeatedly calculating the mapping between the first coordinates system and the second coordinates system using at least partially the registration. The method further comprises repeatedly modifying the external beam radiotherapy system control commands using the mapping.

It is understood that one or more of the aforementioned embodiments of the invention may be combined as long as the combined embodiments are not mutually exclusive.

BRIEF DESCRIPTION OF THE DRAWINGS

In the following preferred embodiments of the invention will be described, by way of example only, and with reference to the drawings in which.

DETAILED DESCRIPTION OF THE EMBODIMENTS

Like numbered elements in these figures are either equivalent elements or perform the same function. Elements which have been discussed previously will not necessarily be discussed in later figures if the function is equivalent.

Figure 1:
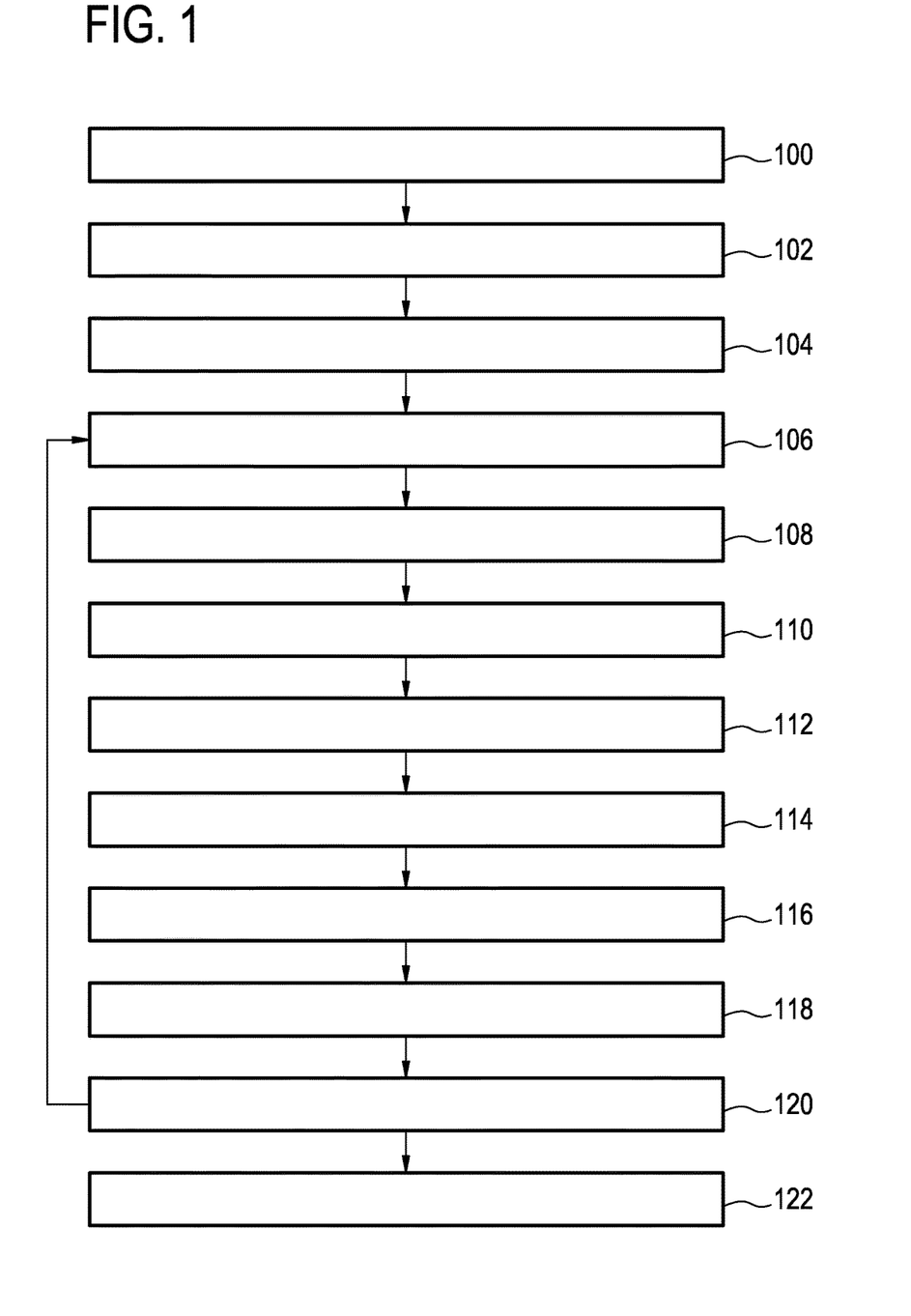
FIG. 1 shows a flow chart which illustrates and example of a method.

FIG. 1 shows a flowchart which illustrates an example of a method of operating a medical instrument. The medical instrument comprises a magnetic resonance imaging system operable for acquiring magnetic resonance data from a subject within the imaging zone. The magnetic resonance imaging system has a first coordinates system. The medical instrument further comprises an external beam radiotherapy system operable for irradiating a target zone and the target zone is within the imaging zone. The external beam radiotherapy system has a second coordinates system. The medical instrument further comprises a radiation beam generation system operable for generating a radiation beam. The medical instrument further comprises a radiation beam detection system operable for acquiring radiation beam detection data descriptive of the radiation beam in the second coordinate system. The method starts with step 100 where planning data descriptive of a spatially dependent radiation dose to the target zone is received. Next in step 102 external beam radiotherapy control commands are generated using the spatially dependent radiation dose. Then in step 104 the irradiation of the target zone is started.

Next in step 106 the external beam radiotherapy system is used to irradiate the target zone using the external beam radiotherapy system control commands. Next in step 108 radiation beams are generated using the radiation beam generation system. Next in step 110 radiation beam detection data is measured using the radiation beam detection system. Next in step 112 the magnetic resonance imaging data is acquired using the magnetic resonance imaging system. Following this in step 114, a magnetic resonance image is generated or reconstructed using the magnetic resonance image data. Then in step 116 the magnetic resonance image is registered to the radiation beam detection data. This registration leads to step 118 which is to calculate a mapping between the first coordinates system and the second coordinates system using the registration. Next in step 120 the external beam radiotherapy system control commands are modified using the mapping. If the irradiation of the subject target zone is complete then the method goes to step 122 which is to end or stop the irradiation of the target zone. If not, the method repeats to step 106 and a loop between steps 106 and 120 is performed until the irradiation is finished 122. Steps 106-120 form a closed loop control loop which account for changes in the divergence between the first coordinates system and the second coordinates system during the irradiation of the target zone.

Figure 2:
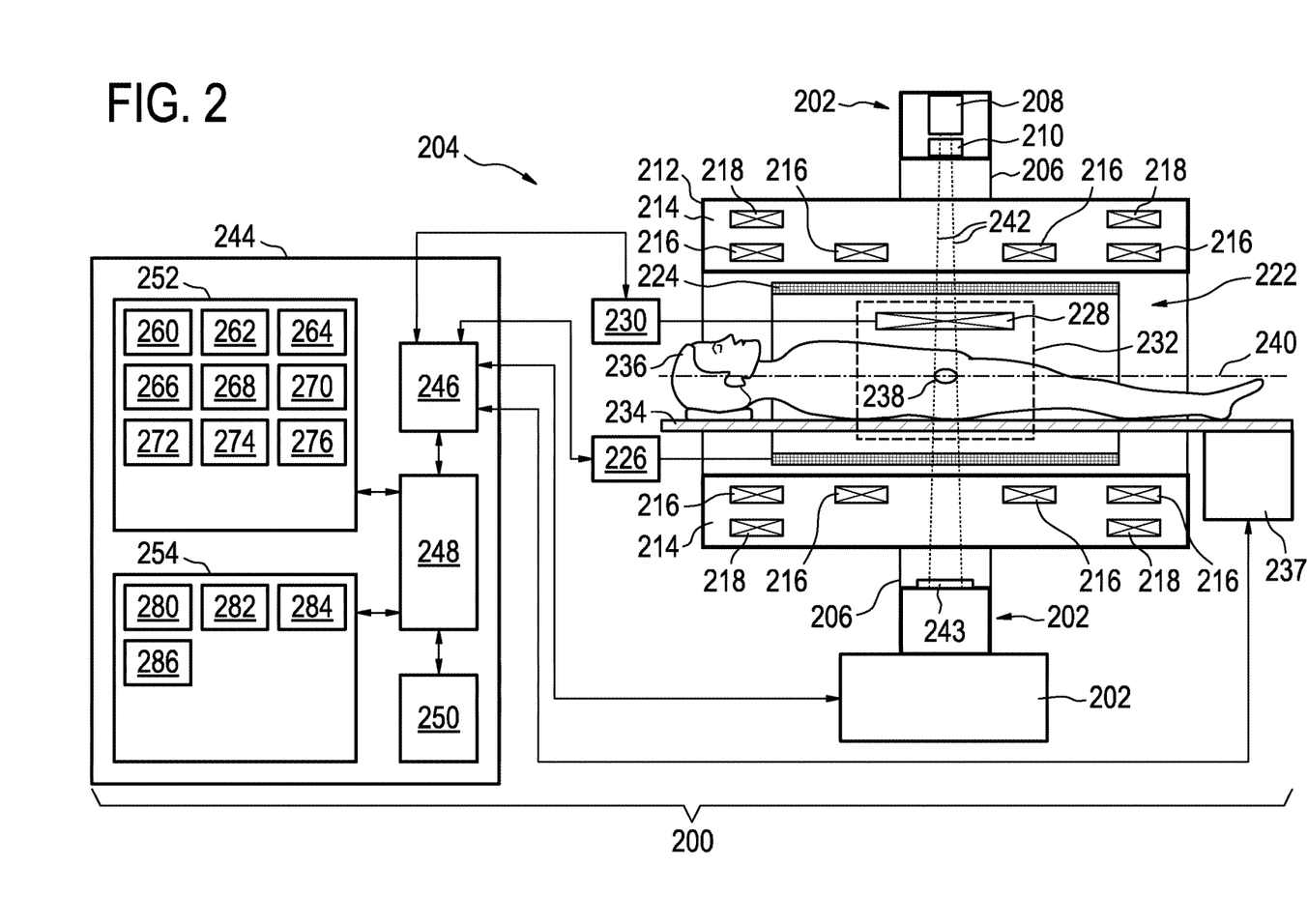
FIG. 2 illustrates an example of a medical instrument.

FIG. 2 shows an example of a medical instrument 200. The medical instrument 200 comprises a external beam radiotherapy system 202 and a magnetic resonance imaging system 204. The external beam radiotherapy system 202 comprises a gantry 206 and a radiotherapy source 208. The gantry 206 is for rotating the radiotherapy source 208 about an axis of gantry rotation 240. Adjacent to the radiotherapy source 208 is a collimator 210. The magnetic resonance imaging system 204 comprises a magnet 212.

It is also possible to use permanent or resistive magnets. The use of different types of magnets is also possible for instance it is also possible to use both a split cylindrical magnet and a so called open magnet. A split cylindrical magnet is similar to a standard cylindrical magnet, except that the cryostat has been split into two sections to allow access to the iso-plane of the magnet, such magnets may for instance be used in conjunction with charged particle beam therapy. An open magnet has two magnet sections, one above the other with a space in-between that is large enough to receive a subject: the arrangement of the two sections area similar to that of a Helmholtz coil. Open magnets are popular, because the subject is less confined. Inside the cryostat of the cylindrical magnet there is a collection of superconducting coils. Within the bore of the cylindrical magnet there is an imaging zone where the magnetic field is strong and uniform enough to perform magnetic resonance imaging.

The magnet 212 shown in this embodiment is a standard cylindrical superconducting magnet. The magnet 212 has a cryostat 214 with superconducting coils within it 216. There are also superconducting shield coils 218 within the cryostat also. The magnet 212 has a bore 222.

Within the bore of the magnet is a magnetic field gradient coil 224 for acquisition of magnetic resonance data to spatially encode proton spins within an imaging zone of the magnet. The magnetic field gradient coil 224 is connected to a magnetic field gradient coil power supply 226. The magnetic field gradient coil 224 is intended to be representative, to allow radiation to pass through without being attenuated it will normally be a split-coil design. Typically magnetic field gradient coils contain three separate sets of coils for spatially encoding in three orthogonal spatial directions. The magnetic field gradient power supply 226 supplies current to the magnetic field gradient coils. The current supplied to the magnetic field coils is controlled as a function of time and may be ramped or pulsed.

There is a radio frequency coil 228 connected to a transceiver 230. The radio frequency coil 228 is adjacent to an imaging zone 232 of the magnet 212. The imaging zone 232 has a region of high magnetic field and homogeneity which is sufficient for performing magnetic resonance imaging. The radio frequency coil 228 may is for manipulating the orientations of magnetic spins within the imaging zone and for receiving radio transmissions from spins also within the imaging zone. The radio frequency coil 228 may also be referred to as an antenna or channel. The radio frequency coil 228 may contain multiple coil elements. The radio frequency antenna may also be referred to as a channel.

The radio frequency coil 228 and radio frequency transceiver 230 may be replaced by separate transmit and receive coils and a separate transmitter and receiver. It is understood that the radio frequency coil and the radio frequency transceiver are representative. The radio frequency antenna is intended to also represent a dedicated transmit antenna and a dedicated receive antenna. Likewise the transceiver may also represent a separate transmitter and receivers.

Also within the bore of the magnet 222 is a subject support 234 for supporting a subject 236. The subject support 234 may be positioned by a mechanical positioning system 237. Within the subject 236 there is a target zone 238. The axis of gantry rotation 240 is coaxial in this particular embodiment with the cylindrical axis of the magnet 212. The subject support 234 has been positioned such that the target zone 238 lies on the axis 240 of gantry rotation. The radiation source 208 is shown as generating a radiation beam 242 which passes through the collimator 203 and through the target zone 238. As the radiation source 208 is rotated about the axis 240 the target zone 238 will always be targeted by the radiation beam 242. The radiation beam 242 passes through the cryostat 214 of the magnet. The magnetic field gradient coil may have a gap which separate the magnetic field gradient coil into two sections. If present, this gap reduces attenuation of the radiation beam 242 by the magnetic field gradient coil 224. In some embodiments the radio frequency coil 228 may also have gaps or be separated to reduce attenuation of the radiation beam 242.

Mounted on the gantry 206 is shown a portal imaging system 243. The portal imaging system 243 is able to acquire an image using the radiation beam 242. As the gantry rotates, the portal imaging system rotates with the radiotherapy source. In this example the magnet 212 is shown as being a cylindrical type magnet and the radiation beam 242 passes through the cryostat 214. A different type of magnet could also be used. A so called split magnet may be divided into two cylindrical sections may be used and the radiation beam 242 may pass through air instead of through the cryostat 214. A so called open magnet which has two toroidal magnets may also be used in step 2. These alternative magnet designs may have the advantage that the radiation beam 242 does not pass through the cryostat 214. This may result in better portal images.

The transceiver 230, the magnetic field gradient coil power supply 226 and the mechanical positioning system 237 are all shown as being connected to a hardware interface 246 of a computer system 244. The computer system 244 is shown as further comprising a processor 248 for executing machine executable instructions and for controlling the operation and function of the therapeutic apparatus. The hardware interface 246 enables the processor 248 to interact with and control the medical instrument 200. The processor 248 is shown as further being connected to a user interface 250, computer storage 252, and computer memory 254.

The computer storage 252 is shown as containing planning data 260. The planning data 260 contains spatially dependent data which describes a desired radiation dose to the target zone 238. The computer storage 252 is further shown as containing a pulse sequence 262. The pulse sequence 262 enables the processor 248 to control the magnetic resonance imaging system 204 to acquire magnetic resonance data. The computer storage 252 is further shown as containing external beam radiotherapy control commands 264 which were generated from the planning data 260. The computer storage 252 is further shown as containing magnetic resonance data 266 that was acquired with the magnetic resonance imaging system 204 using the pulse sequence 262. The computer storage 252 is further shown as containing a magnetic resonance image 268.

The magnetic resonance image 268 was reconstructed from the magnetic resonance data 266. The computer storage 252 is further shown as containing radiation beam detection data 270 that was acquired using the portal imaging system 243. The computer storage 252 is further shown as containing a portal image 272 that was reconstructed from the radiation beam detection data 270. The computer storage 252 is further shown as containing a registration 274 between the portal image 272 and the magnetic resonance image 268. The computer storage 252 is further shown as containing a mapping 276. The mapping 276 is between a first coordinates system of the magnetic resonance imaging system 204 and a second coordinates system belonging to the external beam radiotherapy system 202.

The computer memory 254 is shown as containing a control module. The control module 280 contains computer-executable code which enables the processor 248 to control the operation and function of the medical instrument 200. For instance the control module 280 may enable the processor 248 to use the pulse sequence 262 to acquire the magnetic resonance data 266. The computer memory 254 is further shown as containing control command generation module 282. The control command generation module 282 contains code which enables the processor 248 to generate the external beam radiotherapy control commands 264 from the planning data 260. The control command generation module 282 also contains code which enables the processor 248 to make corrections to the external beam radiotherapy control commands 264 in accordance with or using the mapping 276.

The computer memory 254 is shown as further containing an image reconstruction module 284. The image reconstruction module 284 contains computer-executable code which enables the processor 248 to reconstruct the magnetic resonance image 268 from magnetic resonance data 266 and also the portal image 272 from the radiation beam detection data 270. The computer memory 254 is further shown as containing a registration module 286. The registration module 286 contains computer-executable code which enables the processor 248 to perform image processing tasks such as registering 274 the portal image 272 to the magnetic resonance image 268. The image registration module 286 may be programmed for identifying anatomical landmarks or even identifying the presence of atoms with identifying marks or the silhouette of the subject 236.

Figure 3:
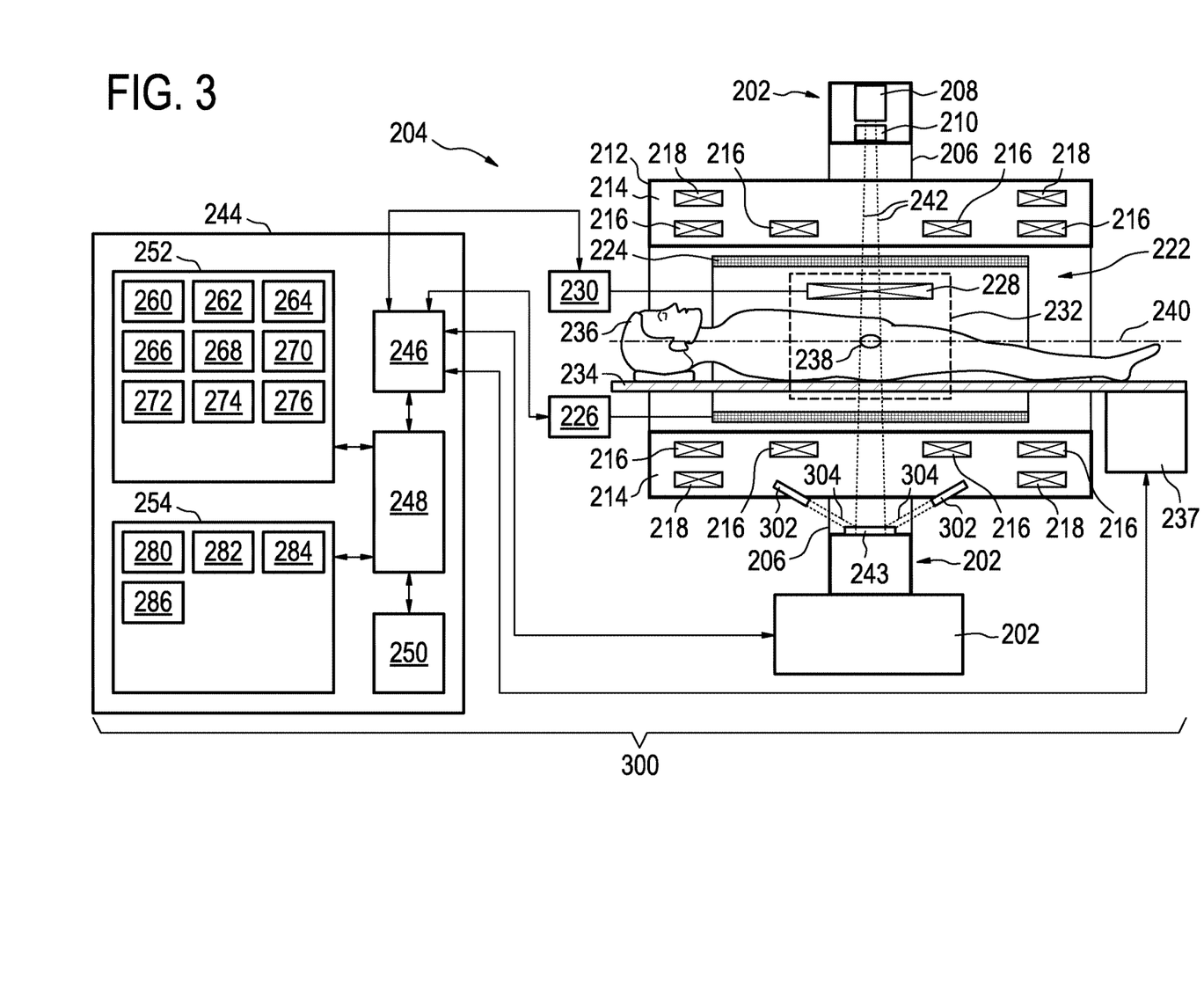
FIG. 3 illustrates a further example of a medical instrument.

FIG. 3 shows a medical instrument 300 similar to that shown in FIG. 2. However, in this embodiment there are two narrow beam X-ray generators 302 shown attached to an exterior surface of the magnet 212. They are aimed such that when they generate a narrow beam X-ray 304 it hits the portal camera 243. From where the image of the narrow beam X-rays 304 show on the portal image 272, a mapping 276 between the first coordinates system and the second coordinates system can be inferred. There may be a number of narrow beam X-ray generators mounted on the magnetic resonance imaging system 204 to account for the rotation of the portal imaging system 243 with the gantry rotates with the radiotherapy source and the portal imaging system.

Figure 4:
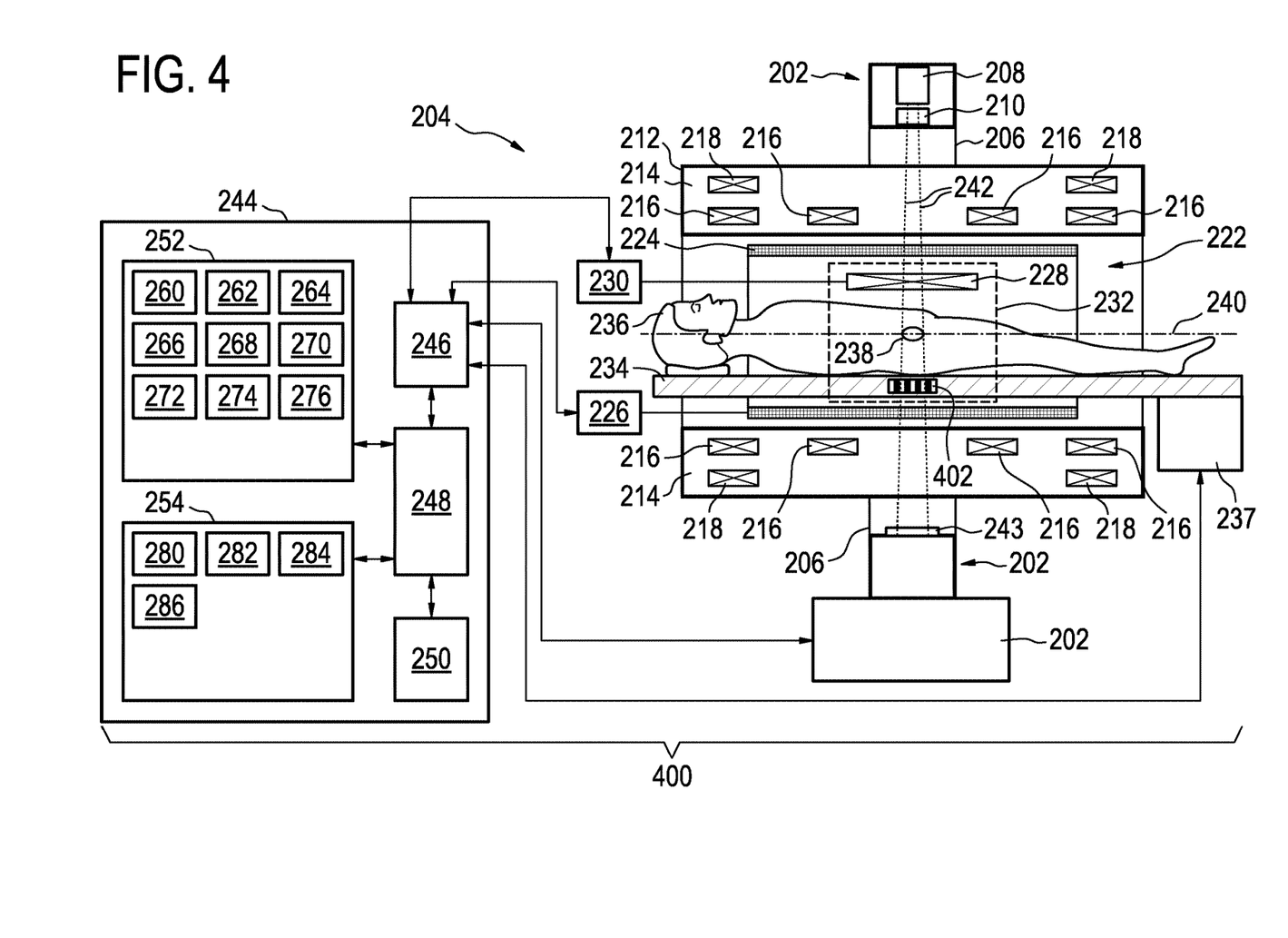
FIG. 4 illustrates a further example of a medical instrument.

FIG. 4 shows a medical instrument 400 shown similar to that in FIGS. 2 and 3. In comparison with FIG. 2, FIG. 4 differs from FIG. 2 in that the subject support 234 contains a phantom 402. The phantom 402 is within the imaging zone 232 and will be visible in the magnetic resonance image 268. The phantom can be constructed of two or more materials that show a contrast in the magnetic resonance image. The two or more materials can also show a contrast in an X-ray type image such that they will be visible in the portal image 272. The radiation beam 242 is shown as passing through the phantom 402. The registration 274 can be determined by comparing the portal image 272 with the magnetic resonance image 268 and noting the location of the phantom 402 in both images.

Figure 5:
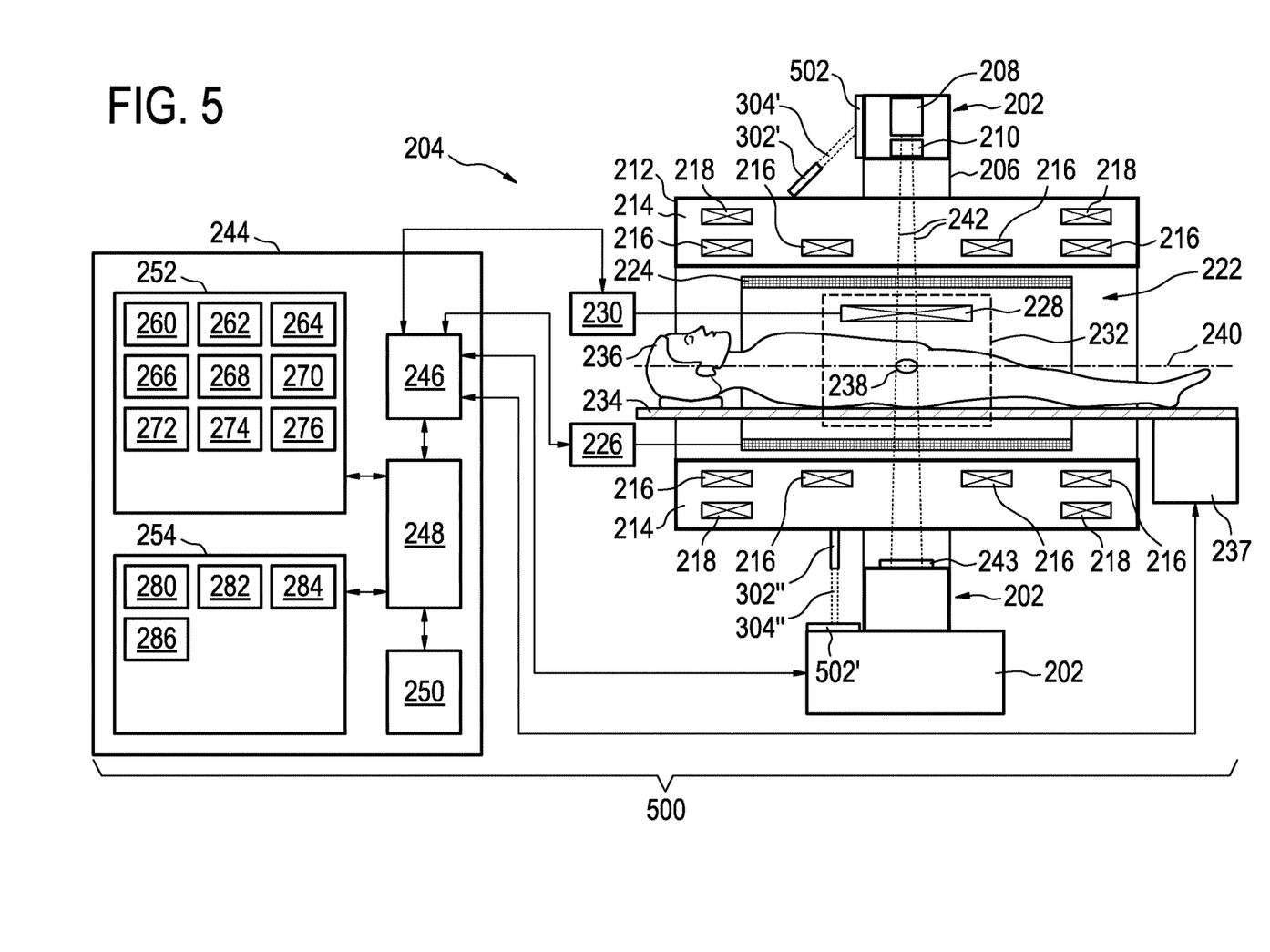
FIG. 5 illustrates a further example of a medical instrument.

FIG. 5 shows a medical instrument 500 that is similar to that shown in FIGS. 2, 3 and 4. In comparison with FIG. 2 the medical instrument 500 in FIG. 5 differs in that there are two narrow beam X-ray generators 302', 302" that are mounted on an exterior surface of the magnet 212. The narrow X-ray beam source 302' produces a narrow beam X-ray source 304' that is aimed at an X-ray detection sensor array 502 mounted on the gantry 206. In some embodiments the sensor array 302 is position fixed relative to the magnet 212 and does not rotate with the gantry 206. In other embodiments there may be a large number of sensors 502 that rotate with the gantry 206. In either case the sensor array 502 can detect the narrow X-ray beam 304' and determine the position of the MRI system 204 relative to that of the external beam radiotherapy system 202. In the case of where there is a large number of sensors 502 and they rotate with the gantry 206 the sensors 502 will also be able to detect the rotational position of the radiotherapy source 208 relative to the coordinates system of the magnet 212. The external beam radiotherapy system 202 also has a base or pedestal which has a second sensor array 502' mounted on it. The narrow X-ray beam source 302" aims the narrow beam X-ray 304" at the second sensor array 302'. The sensor array 502' will also provide data descriptive of the position of the magnetic resonance imaging system 204 relative to the external beam radiotherapy system 202. One or both of the narrow X-ray beam sources 302', 302" may be present.

Figure 6:
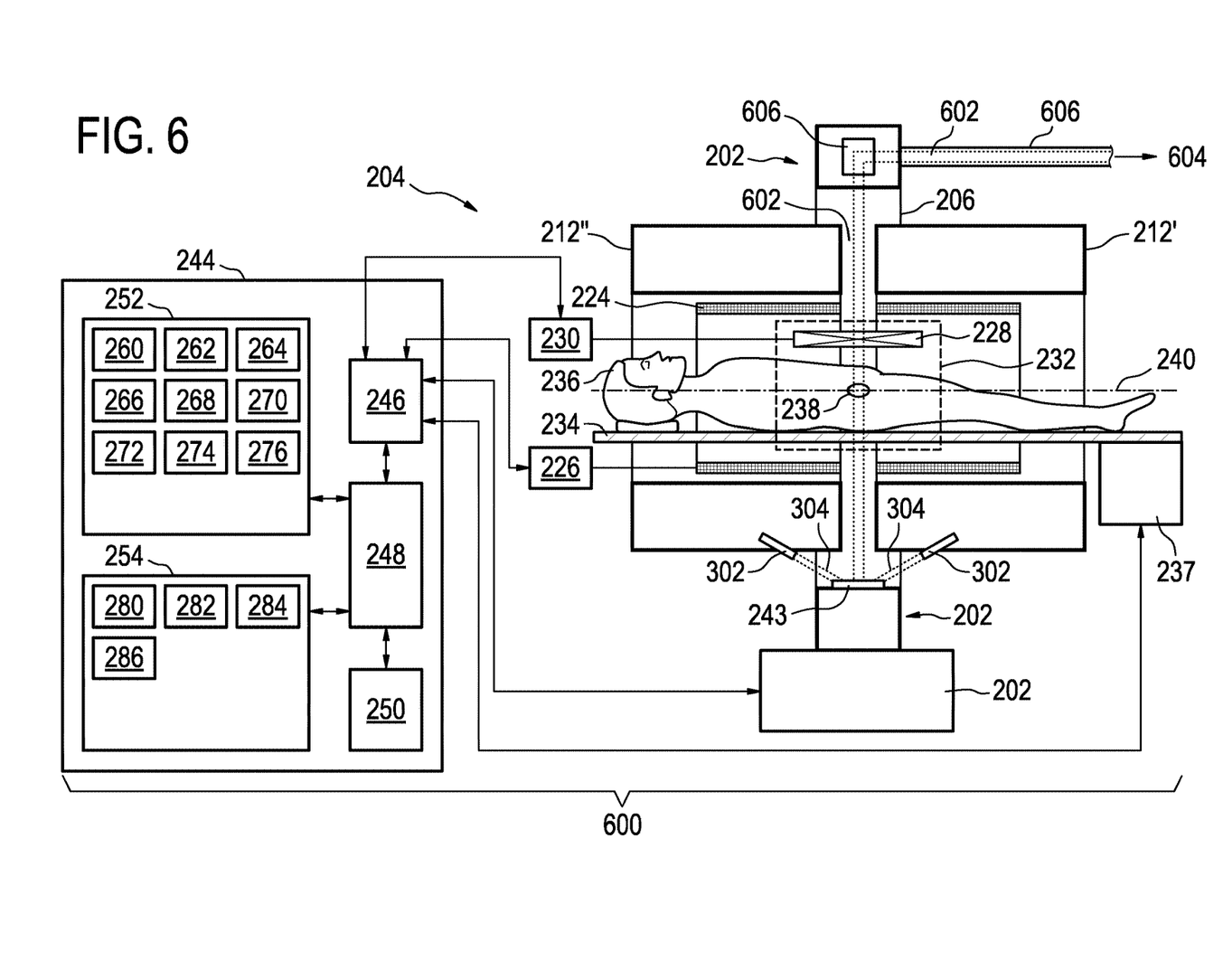
FIG. 6 illustrates a further example of a medical instrument.

FIG. 6 shows a medical instrument 600 that in many ways is similar to the medical instruments shown in FIGS. 2-5. There is a portal imaging system 243 and also optional narrow beam X-ray generators 302. In this example a proton beam 602 is directed towards the target zone 238. The proton beam is provided by a particle accelerator 604 which is not shown in this diagram. Charged particle or proton beam objects 606 take the beam of proton 602 and direct it towards the target zone 238. In this example a so called split magnet is used. The magnet 212', 212" is divided into two halves. The RF coil is also shown as having a gap for the proton beam 602 to travel through. The RF coil 228 and the subject support 234 are not shown as having a gap but they could also have a gap to assist the proton beam 602 traveling with minimal attenuation. In this example the portal camera 243 is used to create rudimentary images of the subject 236 using the radiation generated by the proton beam 602.

Figure 7:
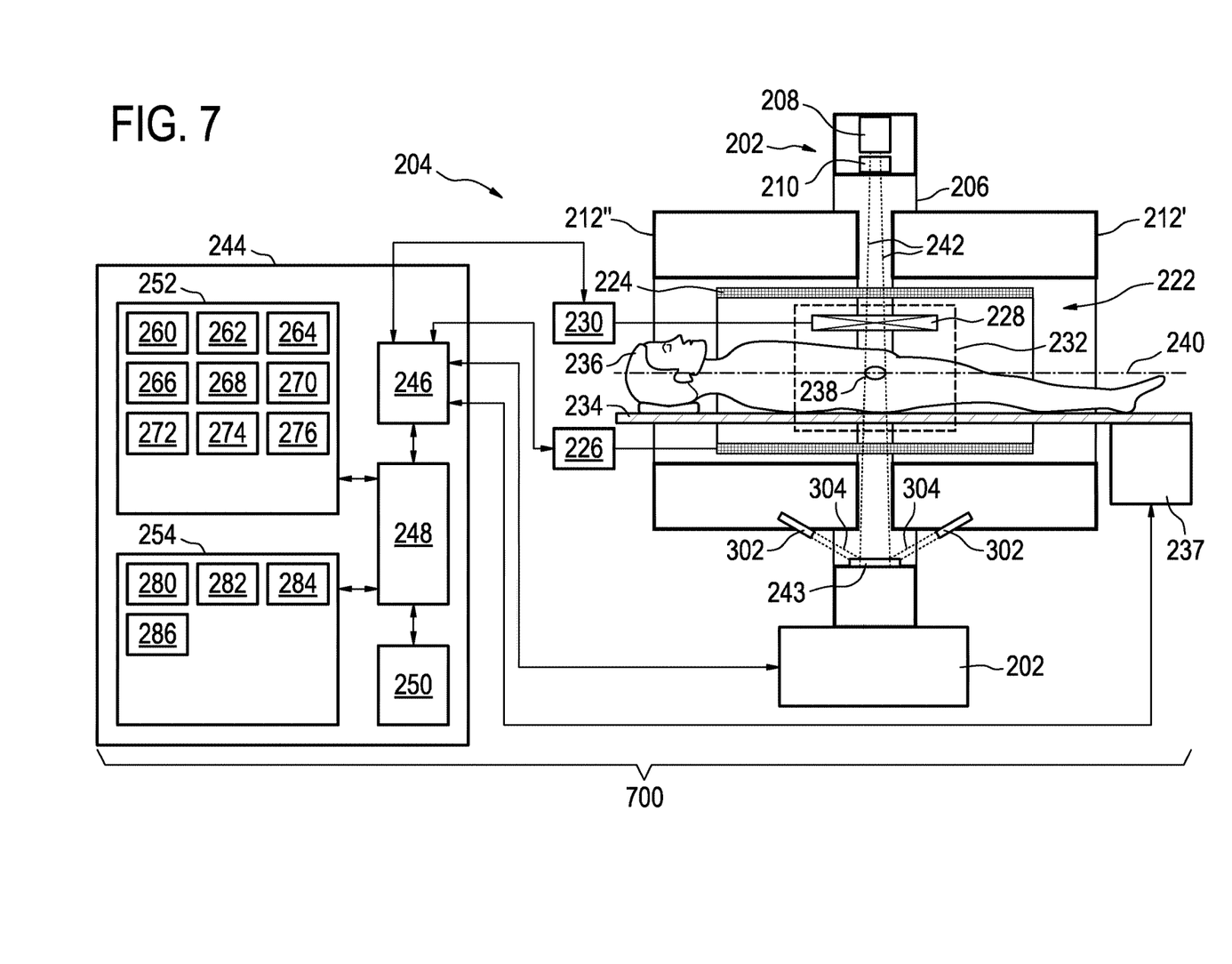
FIG. 7 illustrates a further example of a medical instrument.

FIG. 7 shows an embodiment of a medical instrument 700 similar to that shown in FIG. 3. However, in the example shown in FIG. 7 the split magnet design is used. The magnet is comprised of two halves, 212' and 212". The radiation beam 242 is able to freely pass in the gap between the two halves of the magnet 212', 212".

For an integrated MR-Linac system the precise co-registration between the respective coordinate systems (alignment) is useful for the operation and clinical use. Regulations require a constant quality assurance of such critical system parameters. High standards have to be employed during the design of the system to minimize geometrical tolerances and increase mechanical stability of the system. Large dimensions and size of the system as well as changing ambient parameters (e.g. temperature) however can lead to deviations from a perfect alignment. These deviations would lead to a mismatch between the location of imaged anatomy (MR) and the assumed corresponding location of applied therapeutic irradiation (Linac). This in turn would result in an erroneous treatment. Apart from the obvious possible negative side-effects for the patient this could lead to severe regulatory consequences.

Failure to monitor misalignments of the subsystems of a MR-Linac system (e.g. due to mechanical tolerances, deformations of the system structure, ambient influences) can lead to unnoticed faulty treatments and severe consequences.

Examples of the medical instruments herein may employ image processing means and optionally integrated x-ray navigators to determine and monitor the alignment of the mR's and Linac's coordinate systems. The necessary measurements can be done in a pre-intra- and post-treatment regime. Co-registration of the measured data allows determination of the current transformation between the systems very rapidly. These transformation parameters can then be used to correct the imaging and plan for deviations or stop the treatment.

Employing the x-ray detectors contained within a MR-Linac system and the radiation source an image can be generated (known as portal imaging). Due to the high energy of the radiation and the absorption characteristics of tissue the quality of such images is limited. It is however sufficient to identify landmarks. In conjunction with additional anatomical information (e.g. segmentation of targets, OARs and body outline, patient fixation in known position) corresponding landmarks can be (automatically) identified in MR images. These landmarks can be points or surfaces (based on cone-beam CT portal imaging and 3D MR data).

It is then possible to calculate the (affine) transformation between the two datasets. These transformation parameters can then be used to transform consecutive image data or stop the therapy if the deviation of the alignment becomes too large. This method can be employed before during or after sessions in a short amount of time.

Optionally few small x-ray sources (e.g. miniature design or nano-tube based) can be placed inside/on the MR system (e.g. cryostat) and serve as "navigators" (or sparsely sampled minimal projection "images") and be directed towards the portal imaging detector or few micro-detectors placed on the Linac gantry. Similar to the portal imaging approach this information could then be used for co-registration but without additional patient-dose and imaging time due to portal imaging, allowing real-time monitoring of the correct alignment.

The registration of the coordinate systems also allows to derive the absorption characteristics of the structures for plan adaptation (based on portal imaging) and dose accumulation (Q&A).

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

LIST OF REFERENCE NUMERALS 200 medical instrument
202 external beam radiotherapy system
204 magnetic resonance imaging system
206 gantry
208 radiotherapy source 210 collimator
212 magnet
212' part of split magnet
212" part of split magnet
214 cryostat
216 superconducting coil
218 superconducting shield coil
222 bore
224 magnetic field gradient coil
226 magnetic field gradient coil power supply
228 radio frequency coil
230 transceiver
232 imaging zone
234 subject support
236 subject
237 mechanical positioning system
238 target zone
240 axis of gantry rotation
242 radiation beam
243 portal imaging system
244 computer system
246 hardware interface
248 processor
250 user interface
252 computer storage
254 computer memory
260 planning data
262 pulse sequence
264 external beam radiotherapy control commands
266 magnetic resonance data
268 magnetic resonance image
270 radiation beam detection data
272 portal image
274 registration
276 mapping
280 control module
282 control command generation module
284 image reconstruction module
286 registration module
300 medical instrument
302 narrow beam X-ray generator
302' narrow beam X-ray generator
302" narrow beam X-ray generator
304 narrow beam X-ray
304' narrow beam X-ray
304" narrow beam X-ray
400 medical instrument
402 phantom
500 medical instrument
502 X-ray detection sensor array
502' X-ray detection sensor array
600 medical instrument
601 proton beam source
602 proton beam
604 to particle accelerator
606 proton beam optics
700 medical instrument

The invention claimed is:

1. A medical instrument comprising:
a magnetic resonance imaging system operable for acquiring magnetic resonance data from a subject within an imaging zone, wherein the magnetic resonance imaging system has a first coordinate system;
an external beam radiotherapy system operable for irradiating a target zone, wherein the target zone is within the imaging zone, wherein the external beam radiotherapy system has a second coordinate system;
a radiation beam generation system operable for generating a high-energy radiation beam having a therapeutic effect;
a radiation beam detection system operable for acquiring radiation beam detection data descriptive of the radiation beam in the second coordinate system,
a memory for storing machine executable instructions;
a processor for executing the machine executable instruction, wherein execution of the instructions cause the processor to receive planning data descriptive of a spatially dependent radiation dose to the target zone, wherein execution of the instructions further cause the processor to generate external beam radiotherapy control commands using the spatially dependent radiation dose,
wherein execution of the instructions causes the processor to repeatedly:
control the external beam radiotherapy system to irradiate the target zone using the external beam radiotherapy system control commands;
generate the radiation beams using the radiation beam generation system;
measure the radiation beam detection data using the radiation beam detection system;
acquire the magnetic resonance imaging data using the magnetic resonance imaging system,
generate a magnetic resonance image using the magnetic resonance image data,
determine a registration of the magnetic resonance image to the radiation beam detection data;
calculate a mapping between the first coordinate system and the second coordinate system using the registration; and
modify the external beam radiotherapy system control commands using the mapping and wherein
wherein the radiation beam detection system comprises a portal imaging system for acquiring a portal image of the subject, the portal image being carried by the high-energy radiation beam, in that the radiation beam detection data comprises the portal image, and
execution of the instructions further causes the processor to at least partially calculate the mapping by registering the portal image to the magnetic resonance image.

2. The medical instrument of claim 1, wherein execution of the instructions further cause the processor to control the external beam radiotherapy system to acquire the portal image using radiation passing through the subject.

3. The medical instrument of claim 2, wherein execution of the instructions further causes the processor to:
identify an anatomical landmark of the subject in the portal image;
identify the anatomical landmark in the magnetic resonance image, wherein the registration of the portal image to the magnetic resonance image is performed at least partially using the anatomical landmark.

4. The medical instrument of claim 3, wherein the anatomical land mark is any one of the following: a bone tissue to soft tissue transition, and an implanted fiducial marker, and an external surface of the subject.

5. The medical instrument of claim 4, wherein the magnetic resonance imaging system comprises a subject support, wherein the subject support comprises a phantom, wherein the phantom comprises at least one reference point identifiable in the portal image and the magnetic resonance image, wherein execution of the instructions further causes the processor to at least partially calculate the mapping by registering the at least one reference point in the portal image to the at least one reference point in the magnetic resonance image.

6. The medical instrument of claim 1, wherein the radiation beam generation system comprises a narrow beam X-ray generator for generating a narrow beam X-ray, wherein the narrow beam X-ray generator is attached to the magnetic resonance imaging system, wherein the memory comprises a spatial calibration descriptive of the path of the narrow beam X-ray relative to the field of view of the magnetic resonance imaging system, and wherein the radiation beam detection system is mounted on the external beam radiotherapy system, and wherein the radiation beam detection data is descriptive of the path of the X-ray narrow beam through the X-ray detection system.

7. The medical instrument of claim 6, wherein the magnetic resonance imaging system is operable for supporting the subject away from the path of the narrow beam X-ray.

8. The medical instrument of claim 6, wherein the radiation beam detection system comprises a portal imaging system for acquiring a portal image of the subject during irradiation of the target zone using the external beam radiotherapy system, wherein the portal imaging system is operable for detecting the narrow beam X-ray, wherein execution of the instructions further causes the processor to at least partially calculate the mapping by registering the portal image to the spatial calibration.

9. The medical instrument of claim 6, wherein the radiation beam detection system further comprises an X-ray detection sensor array operable for detecting the path of the narrow beam X-ray through the X-ray detection sensor.

10. The medical instrument of claim 9, wherein the external beam radiotherapy system has an iso-center, wherein the modified external beam radiotherapy system control commands cause the medical instrument to align the iso-center with the target zone.

11. The medical instrument of claim 1, wherein execution of the instructions cause the processor to perform any one or more of the following: control the external beam radiotherapy system to halt irradiating the target zone if the mapping indicates a difference between the first coordinate system and the second coordinate system that is greater than a first predetermined threshold, display a warning message on a display, automatically adjust the irradiation of the external beam radiotherapy system, automatically adjust the acquisition of the magnetic resonance imaging data, control the external beam radiotherapy system to halt irradiating the target zone if a temporal change in the mapping is greater than a second predetermined threshold.

12. The medical instrument of claim 1, wherein the external beam radiotherapy system comprises any one of the following: a proton beam system, and electron beam system, a charged particle beam system, and a linear accelerator.

13. A computer program product comprising machine executable instructions stored on a non-transitory computer readable medium for execution by a processor controlling a medical instrument, wherein the medical instrument comprises a magnetic resonance imaging system operable for acquiring magnetic resonance data from a subject within an imaging zone, wherein the magnetic resonance imaging system has a first coordinate system, wherein the medical instrument further comprises an external beam radiotherapy system operable for irradiating a target zone, wherein the target zone is within the imaging zone, wherein the radiation beam detection system has a second coordinate system, wherein the medical instrument further comprises a radiation beam generation system operable for generating a high-energy radiation beam having a therapeutic effect, wherein the medical instrument further comprises a radiation beam detection system operable for acquiring radiation beam detection data descriptive of the radiation beam in the second coordinate system, wherein execution of the instructions cause the processor to receive planning data descriptive of a spatially dependent radiation dose to the target zone, wherein execution of the instructions further cause the processor to generate external beam radiotherapy control commands using the spatially dependent radiation dose, wherein execution of the instructions causes the processor to repeatedly:
control the external beam radiotherapy system to irradiate the target zone using the external beam radiotherapy system control commands;
generate the radiation beam using the radiation beam generation system;
measure the radiation beam detection data using the radiation beam detection system;
acquire the magnetic resonance imaging data using the magnetic resonance imaging system,
reconstruct a magnetic resonance image using the magnetic resonance image data,
determine a registration between the magnetic resonance image and the radiation beam detection data;
calculate a mapping between the first coordinate system and the second coordinate system using the registration; and
modify the external beam radiotherapy system control commands using the mapping and where
wherein the radiation beam detection system comprises a portal imaging system for acquiring a portal image of the subject, the portal image being carried by the high-energy radiation beam, in that the radiation beam detection data comprises the portal image, and
execution of the instructions further causes the processor to at least partially calculate the mapping by registering the portal image to the magnetic resonance image.

14. A method of operating a medical instrument, wherein the instrument comprises a magnetic resonance imaging system operable for acquiring magnetic resonance data from a subject within an imaging zone, wherein the magnetic resonance imaging system has a first coordinate system, wherein the instrument further comprises an external beam radiotherapy system operable for irradiating a target zone wherein the target zone is within the imaging zone, wherein the radiation beam detection system has a second coordinate system, wherein the instrument further comprises a radiation beam generation system operable for generating a high-energy radiation beam having a therapeutic effect, wherein the instrument further comprises a radiation beam detection system operable for acquiring radiation beam detection data descriptive of the radiation beam in the second coordinate system, wherein the method comprises receiving planning data descriptive of a spatially dependent radiation dose to the target zone, wherein the method further comprises generating external beam radiotherapy control commands using the spatially dependent radiation dose, wherein the method further comprises repeatedly:
controlling the external beam radiotherapy system to irradiate the target zone using the external beam radiotherapy system control commands;
generating the radiation beam using the radiation beam generation system;
measuring the radiation beam detection data using the radiation beam detection system;

acquiring the magnetic resonance imaging data using the magnetic resonance imaging system,
reconstruct a magnetic resonance image using the magnetic resonance image data,
determine a registration between the magnetic resonance image and the radiation beam detection data;
calculating a mapping between the first coordinate system and the second coordinate system using the registration; and
modifying the external beam radiotherapy system control commands using the mapping
and where
the external beam radiotherapy system comprises a radiation beam source for irradiating the target zone, wherein the radiation beam generation system comprises the radiation beam source, wherein the radiation beam detection system comprises a portal imaging system for acquiring a portal image of the subject, the portal image being carried by the high-energy radiation beam, wherein the radiation beam detection data comprises the portal image, wherein execution of the instructions further causes the processor to at least partially calculate the mapping by registering the portal image to the magnetic resonance image.

* * * * *